(12) United States Patent
Jang et al.

(10) Patent No.: US 9,925,328 B2
(45) Date of Patent: Mar. 27, 2018

(54) BALLOON CATHETER

(75) Inventors: Yang Soo Jang, Seoul (KR); Myeong Ki Hong, Seoul (KR); Byeong Keuk Kim, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 559 days.

(21) Appl. No.: 14/239,852

(22) PCT Filed: Aug. 21, 2012

(86) PCT No.: PCT/KR2012/006616
§ 371 (c)(1),
(2), (4) Date: Feb. 20, 2014

(87) PCT Pub. No.: WO2013/027990
PCT Pub. Date: Feb. 28, 2013

(65) Prior Publication Data
US 2014/0180086 A1    Jun. 26, 2014

(30) Foreign Application Priority Data

Aug. 22, 2011 (KR) .................. 10-2011-0083548
Aug. 17, 2012 (KR) .................. 10-2012-0089980

(51) Int. Cl.
*A61M 25/10* (2013.01)
*A61M 5/00* (2006.01)
*A61M 25/00* (2006.01)

(52) U.S. Cl.
CPC ............ *A61M 5/007* (2013.01); *A61M 25/10* (2013.01); *A61M 2025/0059* (2013.01)

(58) Field of Classification Search
CPC .................. A61M 5/007; A61M 25/10; A61M 2025/0059; A61M 2025/018;
(Continued)

(56) References Cited

U.S. PATENT DOCUMENTS 4,896,670 A    1/1990  Crittenden
5,154,725 A    10/1992 Leopold
(Continued)

FOREIGN PATENT DOCUMENTS

EP    0875263 A3    7/1999
JP    20010269410 A2  10/2001
(Continued)

OTHER PUBLICATIONS

Chinese Patent Office, Office Action dated Mar. 10, 2016 against the corresponding Chinese Application No. 201280041224.6.
(Continued)

*Primary Examiner* — Corrine McDermott
*Assistant Examiner* — Tin Nguyen
(74) *Attorney, Agent, or Firm* — Hammer & Associates, P.C.

(57) ABSTRACT

The present invention relates to a balloon catheter. The invention comprises: a first shaft; an expandable balloon which is attached to the front end of the first shaft; an expandable lumen which is formed inside the first shaft and to which a liquid required for expanding the balloon is provided; a second shaft which extends from the front end of the first shaft to which the balloon is attached and has a wire hole through which a guide wire passes; and a guide wire lumen, which is formed inside the second shaft and through which the guide wire passes. According to the invention, the first and second shafts are coaxially connected and the expandable lumen and the guide wire lumen are respectively formed in each shaft in order to reduce the overall diameter of the shaft, thereby facilitating surgery and improving pushability.

6 Claims, 6 Drawing Sheets

(58) Field of Classification Search
CPC .. A61M 2025/1056; A61M 2025/0183; A61M 2025/1063; A61M 2025/1061; A61M 25/0029; A61M 25/1006; A61M 25/1025; A61M 25/1002
See application file for complete search history.

(56) References Cited

U.S. PATENT DOCUMENTS

| | | | |
|---|---|---|---|
| 5,395,332 | A | 3/1995 | Ressemann et al. |
| 5,545,134 | A | 8/1996 | Hilaire et al. |
| 6,491,662 | B1 | 12/2002 | Liprie et al. |
| 2002/0151871 | A1* | 10/2002 | Gaiser ................ A61B 1/00154 604/510 |
| 2004/0267196 | A1* | 12/2004 | Miki ................. A61M 25/1025 604/103.04 |
| 2005/0124939 | A1* | 6/2005 | Konstantino ....... A61M 25/104 604/194 |
| 2008/0077085 | A1* | 3/2008 | Eidenschink ......... A61M 25/10 604/96.01 |

FOREIGN PATENT DOCUMENTS

| | | |
|---|---|---|
| JP | 20010517503 T2 | 10/2001 |
| JP | 20030250898 A2 | 9/2003 |
| JP | 20070512931 | 5/2007 |
| KR | 1020040079425 | 9/2004 |
| KR | 1020070055598 | 5/2007 |
| KR | 1020080110224 | 12/2008 |
| KR | 1020090029432 | 3/2009 |
| KR | 1020110088841 | 8/2011 |

OTHER PUBLICATIONS

Japanese Patent Office, Notice of Reasons for Rejection, Office Action dated Jan. 26, 2015 against the corresponding Japanese Application No. 2014-527065.

Chinese Patent Office, Office Action dated Jun. 23, 2015 against the corresponding Chinese Application No. 201280041224.6.

* cited by examiner

[Figure 1]
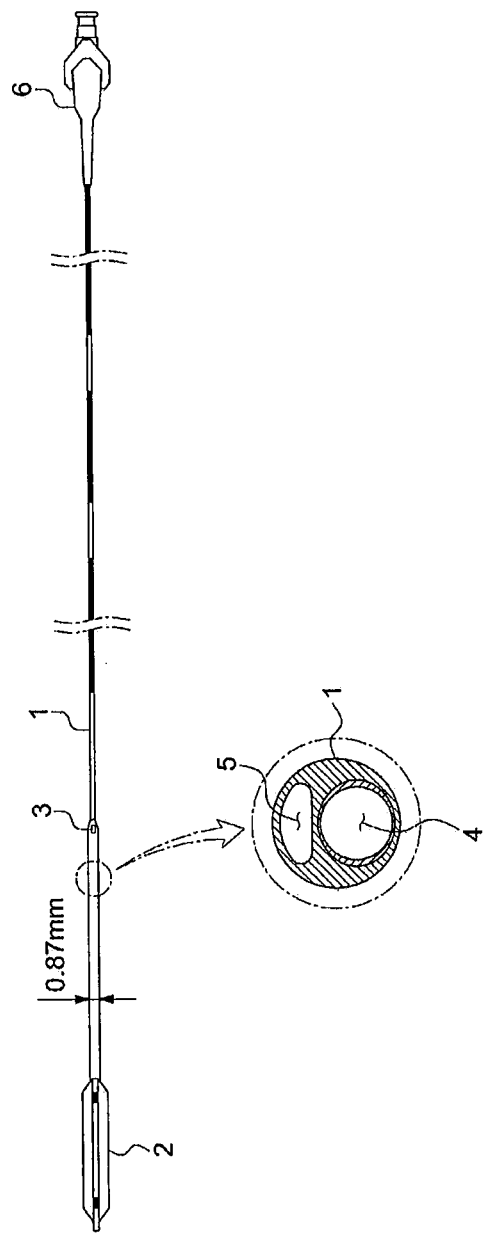

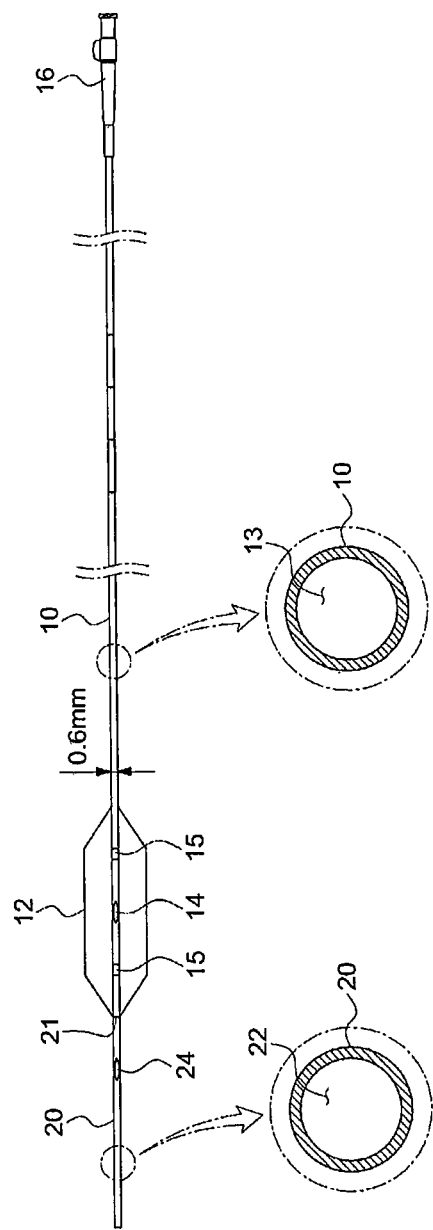
[Figure 2]

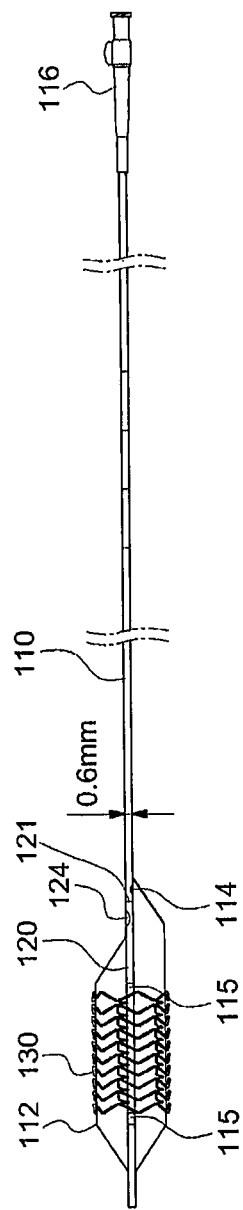
[Figure 3]

【Figure 4】
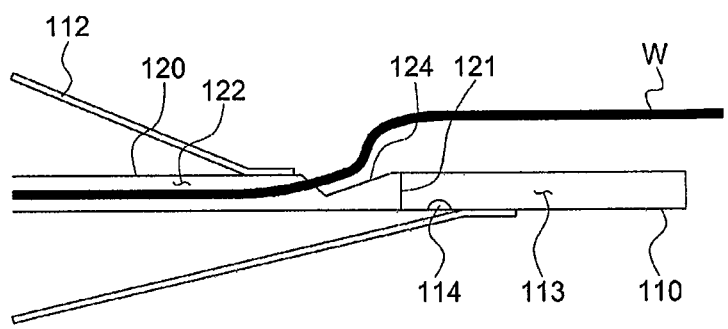

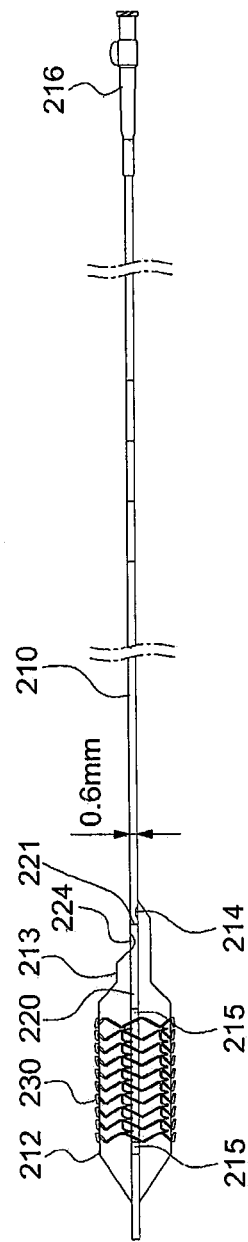
[Figure 5]

【Figure 6】
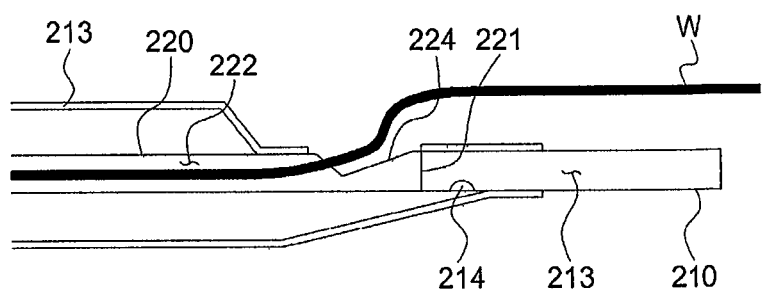

BALLOON CATHETER

CROSS-REFERENCE TO RELATED APPLICATION

This application claims priority to and the benefit of Korean Patent Application No. 10-2011-0083548, filed Aug. 22, 2011, and Korean Patent Application No. 10-2012-0089980, filed Aug. 17, 2012, the disclosure of which is incorporated herein by reference in its entirety.

TECHNICAL FIELD

The present invention relates to a balloon catheter and, more particularly, to a balloon catheter in which an expansion lumen to which liquid for the expansion of a balloon is supplied and a guide wire lumen through which a guide wire passes are configured not to overlap with each other and the diameter of a shaft is reduced, thereby enabling easy transfer to a limited space of a guide catheter, smoothing the injection of a contrast medium when a surgical procedure is performed since a sufficient space can be secured, and capable of improving pushability by which two or more balloon catheters can enter at the same time.

BACKGROUND ART

In general, a balloon catheter and a stent are medical tools surgically installed within a lumen or blood vessel and configured to expand the lumen or blood vessel when a disease is generated, such as when the unique function of a lumen within the human body is reduced due to the lumen narrowed by various types of diseases generated within the human body or when the circulation of the blood becomes poor due to a narrowed blood vessel.

A coronary artery disease or an ischemic heart disease is a disease generated because fat-forming elements are deposited on the wall of a coronary artery blood vessel, the lumen of the coronary artery is gradually narrowed as an inflammatory response accompanied by the deposition, and the blood is not sufficiently supplied to the heart muscle due to the narrowed lumen size of the coronary artery.

If the blood is not sufficiently supplied to the heart muscle, a pain in the chest, a difficulty in breathing, and other symptoms are generated depending on a degree thereof. Such a coronary artery disease appears as a clinical sign, such as angina, acute myocardial infarction, or a sudden heart failure.

Percutaneous Coronary Intervention (PCI) is a treatment method of physically expanding the lumen of the coronary artery that has been narrowed because cholesterol is deposited on a blood vessel wall using a balloon catheter or a stent.

FIG. 1 is a side view showing a conventional balloon catheter. Referring to FIG. 1, a balloon 2 is provided at the front end of the shaft 1 of the conventional balloon catheter. The balloon 2 may be attached to the front end of the shaft 1 using adhesives, etc.

Meanwhile, a wire discharge hole 3 through which a guide wire is discharged is formed on one side of the shaft 1. As described above, in the existing balloon catheter, the cross section of the shaft 1 in which the wire discharge hole 3 is formed is described below. As shown in FIG. 1, a guide wire lumen 4 through which a guide wire passes and an expansion lumen 5 are together formed within the shaft 1.

That is, the guide wire is inserted into the front end (opened) of the balloon catheter and discharged to the wire discharge hole 3 after passing through the guide wire lumen 4 so that the balloon catheter enters and exits along the guide wire. Liquid (i.e., a solution for the transfer of pressure, for example, a contrast medium and a mixture of saline) for expanding the balloon 2 is supplied to the expansion lumen 5. The liquid for expansion is supplied through a connection port 6 provided at the rear end of the shaft 1. The connection port 6 is a port connected to an expansion-contraction device.

However, the aforementioned prior art has the following problems.

The conventional balloon catheter is problematic in that the diameter of the shaft 1 is generally increased because the guide wire lumen 4 and the expansion lumen 5 are overlapped with each other and formed in the shaft 1. If the diameter of the shaft 1 is increased as described above, pushability is lowered when a surgical operator performs a surgical procedure on the catheter, making the surgical procedure difficult. In particular, there is a problem in that a surgical procedure for a tortuous blood vessel, such as the heart blood vessel, is difficult.

Furthermore, if the guide wire lumen 4 and the expansion lumen 5 are formed together, there is a problem in that the time taken to expand and contract the balloon 2 becomes long because the diameter of the expansion lumen 5 is inevitably relatively reduced.

DISCLOSURE

Technical Problem

Accordingly, the present invention has been made to solve the aforementioned conventional problems, and an object of the present invention is to provide a balloon catheter capable of improving pushability by relatively reducing the diameter of the shaft of a balloon catheter and minimizing the time taken to expand and contract a balloon.

Technical objects to be achieved by the present invention are not limited to the aforementioned object, and other technical objects that have not been described above will become evident to those skilled in the art to which the present invention pertains from the following description.

Technical Solution

In accordance with an aspect of the present invention for achieving the above object, the present invention provides a balloon catheter, including a first shaft; a balloon attached to the front end of the first shaft and being expandable; an expansion lumen formed within the first shaft and supplied with liquid necessary to expand the balloon; a second shaft coaxially extended from the front end of the first shaft to which the balloon has been attached and having a wire discharge hole from which a guide wire is discharged formed in the second shaft; and a guide wire lumen formed within the second shaft and having the guide wire pass through the guide wire lumen, wherein the expansion lumen and the guide wire are separated.

A hub installed at the rear end of the first shaft and combined with a pressurization device for supplying the liquid is further included.

One or more pressure injection ports for injecting the liquid into the balloon are formed in the first shaft.

The pressure injection ports are formed at respective positions corresponding to the front end and rear end of the balloon.

One or more radiopaque markers are formed in the first shaft.

The marker is further formed at the front end of the second shaft.

The first shaft and the second shaft are integrally fabricated, and a blocking medium is installed between the first shaft and the second shaft.

In accordance with another aspect of the present invention, the present invention provides a balloon catheter, including a first shaft; an expansion lumen formed within the first shaft and supplied with liquid necessary to expand a balloon; a second shaft extended from the front end of the first shaft; a guide wire lumen formed within the second shaft and having a guide wire pass through the guide wire lumen; and the balloon having the front end attached to the second shaft and being expandable and having part of the rear end attached to the front end of the first shaft, wherein a pressure injection port is formed in the first shaft corresponding to a front of portion to which the balloon has been attached and the liquid is injected into the balloon through the pressure injection port, and a wire discharge hole is formed in the second shaft corresponding to a rear of the portion to which the balloon has been attached and the guide wire is discharged through the wire discharge hole.

In accordance with yet another aspect of the present invention, a balloon catheter includes a first shaft in which an expansion lumen to which a fluid necessary to expand a balloon is supplied is formed; a second shaft extended from the front end of the first shaft and having a guide wire lumen through which a guide wire passes formed in the second shaft; and the balloon attached to the first shaft or the second shaft and being expandable.

Advantageous Effects

In accordance with the present invention, the first shaft and the second shaft are connected coaxially, and the expansion lumen and the guide wire lumen are formed in each of the shafts. Accordingly, there are advantages in that a surgical procedure becomes facilitated and pushability is improved because the diameter of the shaft is generally reduced.

Furthermore, there is an advantage in that the time taken to expand and contract a balloon can be reduced because the diameter of the expansion lumen is relatively increased due to only one lumen present in a single shaft.

DESCRIPTION OF DRAWINGS

FIG. 1 is a side view showing a conventional balloon catheter.

FIG. 2 is a side view showing a balloon catheter in accordance with an embodiment of the present invention.

FIG. 3 is a side view showing a balloon catheter in accordance with another embodiment of the present invention.

FIG. 4 is an enlarged side view showing major elements of the balloon catheter in accordance with another embodiment of the present invention.

FIG. 5 is a side view showing a balloon catheter in accordance with yet another embodiment of the present invention.

FIG. 6 is an enlarged side view showing major elements of the balloon catheter in accordance with yet another embodiment of the present invention.

MODE FOR INVENTION

Hereinafter, an embodiment of a balloon catheter according to the present invention is described in detail with reference to the accompanying drawings. In terms used herein, the 'front' means the bottom on the basis of FIG. 2, that is, the direction along which the balloon catheter is inserted, and 'the rear' means the top on the basis of FIG. 2, that is, the direction opposite the direction along which the balloon catheter is inserted. Furthermore, a term 'front end' means an end that is placed at the front in the balloon catheter, and a term 'rear end' means an end that is placed at the back in the balloon catheter.

FIG. 2 is a side view showing a balloon catheter in accordance with an embodiment of the present invention.

Referring to FIG. 2, the balloon catheter according to the present invention basically includes a first shaft 10; a balloon 12 attached to the front end of the first shaft 10; and a second shaft 20 coaxially extended from the front end of the first shaft 10 to which the balloon 12 has been attached.

The first shaft 10 and/or the second shaft 20 are made in a braided form in order to improve the torque of the balloon catheter and are subject to hydrophilic coating in order to reduce a friction with the internal wall of the blood vessel. The balloon 12 can be attached to the front end of the first shaft 10 by way of attachment means using adhesives, heat, or a laser, and the front end and the rear end of the balloon 12 can be attached. The balloon 12 may be attached to the first shaft 10 or may be overlapped with the first shaft 10 and the second shaft 20. The balloon 12 functions to slowly expand in the state in which a stent (not shown) has been attached to the outer circumferential surface of the balloon 12 and to closely adhere the stent to the internal wall of the blood vessel.

An expansion lumen 13 is formed within the first shaft 10. The expansion lumen 13 is a passage through which liquid (i.e., a solution for the transfer of pressure, for example, a contrast medium or a mixture of saline) supplied from a hub 16 is supplied. The hub 16 is combined with an expansion-contraction device (not shown). The expansion-contraction device functions to expand the balloon 12 by pressurizing and supplying the liquid. In the present embodiment, only the expansion lumen 13 is formed within the first shaft 10, but a guide wire lumen 22 is not formed within the first shaft 10. This is described in more detail below.

Furthermore, a pressure injection port 14 is formed at the front end of the first shaft 10 to which the balloon 12 has been attached. The pressure injection port 14 is a portion through which liquid supplied through the expansion lumen 13 is injected into the balloon 12. One or more pressure injection ports 14 may be formed in the first shaft 10. For example, if the pressure injection ports 14 are formed at respective portions corresponding to the front end and the rear end of the balloon 12, the balloon 12 can be generally spread at the same time without being expanded irregularly.

Furthermore, one or more markers 15 may be formed in the first shaft 10. The marker 15 is made of radiopaque materials and is a portion formed to easily check the position of the balloon catheter when a surgical procedure is performed. The marker 15 may be made of radiopaque metal or resin and may be made of one or more selected from the group that consists of stainless steel, gold, platinum, tin, tungsten, and lead, for example.

Meanwhile, the marker 15 has been illustrated as being formed only in the first shaft 10, but the present invention is not limited thereto. The marker 15 may be formed at the front end of the second shaft 20.

Next, the second shaft 20 is coaxially extended from the front end of the first shaft 10. In the present embodiment, the first shaft 10 and the second shaft 20 need to be connected so that the respective lumens 13 and 22 are blocked without communicating with each other. To this end, a blocking medium 21 may be installed between the first shaft 10 and the second shaft 20. For example, the second shaft 20 may be integrally formed with the first shaft 10, and the blocking medium 21 may be installed at the portion where the first shaft 10 and the second shaft 20 are connected. Furthermore, the second shaft 20 may be fabricated separately from the first shaft 10, and the second shaft 20 may be combined with the first shaft 10 in the state in which any one end of the second shaft 20 has been blocked.

The guide wire lumen 22 through which a guide wire passes is formed within the second shaft 20. The guide wire lumen 22 is a portion through which the guide wire inserted into the guide wire lumen 22 passes. In the present embodiment, the first shaft 10 and the second shaft 20 do not communicate with each other, and the expansion lumen 13 and the guide wire lumen 22 are isolated from each other. Accordingly, there is an advantage in that the diameter of a shaft can be minimized because only one of the lumens 13 and 22 is placed in one shaft without overlapping between the two lumens 13 and 22.

In the conventional balloon catheter, the diameter of the shaft is 0.87 mm as shown in FIG. 1, whereas in the balloon catheter according to the present invention, the diameter of the shaft can be reduced to 0.6 mm as shown in FIG. 2. Such a change of the diameter may be different depending on the size of a guide wire used, and the illustrated numerical value is a numerical value when a 0.014" guide wire is used. Accordingly, since the balloon catheter can be reduced in size, mobility can become better and pushability can be improved in a tortuous blood vessel, such as the heart blood vessel. Furthermore, since the shape of the balloon catheter is reduced, a kissing balloon technique and kissing stenting are made possible using a 5F guiding catheter. Furthermore, a transradial approach rather than a transfemoral approach can become more active in the future because a difficulty of contrast injection, that is, the greatest problem when performing stenting using the 5F guiding catheter, can be overcome.

Furthermore, the diameter of the expansion lumen 13 is relatively increased as compared with the prior art because only one of the lumens 13 and 22 is placed in a single shaft. Accordingly, the time taken to expand and contract the balloon 12 can be reduced because a greater amount of liquid can be injected or discharged. Furthermore, a guide wire can be easily inserted because the diameter of the guide wire lumen 22 is relatively increased.

Meanwhile, a wire discharge hole 24 from which the guide wire is discharged is formed at the rear end of the second shaft 20. The guide wire is inserted through the front end (opened) of the second shaft 20 and discharged through the wire discharge hole 24, so the guide wire functions to enable the balloon catheter to easily enter or exit along the guide wire. That is, the guide wire is inserted so that it passes through the guide wire lumen 22 and discharged to the front end of the second shaft 20.

A process of performing a surgical procedure on the balloon catheter having the above construction according to the present invention is described below. In a blood vessel balloon plastic operation, the insertion of the balloon catheter is started in the state in which the guide wire has been previously inserted. The balloon catheter is inserted along the guide wire until it reaches a lesion or an isthmus to be treated. When the balloon catheter reaches the lesion or the isthmus, a surgical operator supplies liquid through the hub 16 combined with a pressurization device, and thus the balloon 12 is expanded by the liquid injected through the pressure injection port 14. The expanded balloon 12 widens a narrowed blood vessel, making a blood flow smooth. Here, it may be expected that the guide wire present outside the balloon 12 induces a crack atherosclerotic plaques that have been much calcareous.

Furthermore, a stent is inserted into the blood vessel in the state in which the stent has been contracted on the outside of the balloon 12 and then expanded at the lesion or the isthmus, thereby enabling the treatment of the lesion. Here, the balloon 12 may be expanded in the state in which the guide wire has been inserted, that is, in the state in which the guide wire is present outside the stent, or the balloon 12 may be expanded in the state in which the guide wire has been pulled out after the stent is placed.

Another embodiment of the present invention is described below with reference to FIGS. 3 and 4. FIG. 3 is a side view showing a balloon catheter in accordance with another embodiment of the present invention, and FIG. 4 is an enlarged side view showing major elements of the balloon catheter in accordance with another embodiment of the present invention.

In the present embodiment, a guide wire has been configured to be discharged from the rear of a balloon without being discharged from the front of the balloon as in the embodiment of FIG. 2. The same reference numerals to each of which a hundred is added are assigned to the same or similar elements as those of the aforementioned embodiment, and a detailed description of the elements is omitted for convenience of description.

Referring to FIG. 3, an expansion lumen 113 is formed within a first shaft 110, a pressure injection port 114 is formed at the front end of the first shaft 110, and a guide wire lumen 122 is formed within a second shaft 120.

In the embodiment of FIG. 2, the boundary of the first shaft 10 and the second shaft 20 is placed at the front end of the balloon 12 or in front of the pressure injection port 14. Unlike in the embodiment of FIG. 2, in FIG. 3, the boundary of the first shaft 110 and the second shaft 120 is placed in front of the pressure injection port 114 and at the back of the rear end of the balloon 112.

Meanwhile, in the present embodiment, the upper and lower parts of a balloon 112 are attached to the different shafts 110 and 120. For reference, the upper part of the balloon 112 refers to a portion that is placed on the upper side on the basis of the shafts 110 and 120, and the lower part of the balloon 112 refers to a portion that is placed on the lower side on the basis of the shafts 110 and 120. Here, the balloon 112 may have a shape, such as a spherical shape, an elliptical shape, a conical shape, or a balloon shape having a dual diameter (i.e., a stepped balloon), in addition to the shape shown in FIG. 3.

The front end and the rear end of the balloon 112 at the upper part of the balloon 112 are attached to the second shaft 120, but the front end of the balloon 112 is attached to the second shaft 120 and the rear end of the balloon 112 is attached to the first shaft 110 at the lower part of the balloon 112. That is, the front ends of the balloon 112 on the upper and lower parts of the balloon 112 are attached to the same position, but the rear ends of the balloon 112 on the upper and lower parts of the balloon 112 are attached to different positions. Since the upper and lower parts of the balloon 112 are divided and attached to the first shaft 110 and the second shaft 120 as described above, the expansion lumen 113 and the guide wire lumen 122 can be separated from each other.

Referring to FIG. 4, the rear end of the balloon 112 on the lower side of the balloon 112 is attached to the first shaft 110 that corresponds to the rear than to the pressure injection port 114. Accordingly, liquid injected into the pressure injection port 114 expands the balloon 112.

Meanwhile, a wire discharge hole 124 from which a guide wire W is discharged is formed at the rear end of the second shaft 120. Furthermore, the wire discharge hole 124 does not interfere with the balloon 112 because it is formed in the second shaft 120 corresponding to the rear of the balloon 112 attached to the second shaft 120. Accordingly, the second shaft 120 substantially traverses the inside of the balloon 112 and extends, and the guide wire W also traverses the inside from the rear of a portion to which the balloon 112 has been attached and the passes therethrough.

Here, the position where the balloon 112 has been attached has been illustrated as being divided into the upper and lower parts, but the balloon 112 is substantially formed integrally and the side parts of the balloon 112 connect the upper and lower parts attached to the respective shafts 110 and 120. Furthermore, the balloon 112 does not need to be necessarily attached as shown in FIG. 4, and the upper and lower parts of the balloon 112 may be attached to the shafts 110 and 120 in opposite ways or at different angles. Furthermore, in fabricating the balloon 112, the balloon 112 may be divided into upper and lower parts, and the two halves of the balloon 112 having different sizes may be first fabricated and attached using a laser and the balloon 112 may be fabricated using a molding having a special form.

Furthermore, in the present embodiment, a blocking medium 121 is placed in the rear of the balloon 112, whereas in the embodiment of FIG. 2, the blocking medium 21 is placed in front of the balloon 12.

Meanwhile, a stent 130 is provided on the outer circumferential surface of the balloon 112, thus being capable of transferring the balloon catheter to a lesion or an isthmus.

A process of performing a surgical procedure on the balloon catheter according to the present embodiment is substantially the same as the surgical procedure of the aforementioned embodiment.

As described above, in the balloon catheter according to the present invention, the expansion lumen (13,113) and the guide wire lumen (22,122) have only to be blocked and formed in the first shaft (10,110) and the second shaft (20,120), respectively, and the present invention is not limited to the aforementioned embodiment.

Meanwhile, the diameters and physical properties of the first shaft (10,110) and the second shaft (20,120) described above may be different.

Yet another embodiment of the present invention is described below with reference to FIGS. 5 and 6. FIG. 5 is a side view showing a balloon catheter in accordance with yet another embodiment of the present invention, and FIG. 6 is an enlarged side view showing major elements of the balloon catheter in accordance with yet another embodiment of the present invention. The same reference numerals to each of which two hundred is added are assigned to the same or similar elements as those of the aforementioned embodiment, and a detailed description of the elements is omitted for convenience of description.

In the present embodiment, a balloon (212,213) has a balloon shape having a dual diameter (i.e., a stepped balloon) including a first expansion unit 212 and a second expansion unit 213 having a smaller diameter than the first expansion unit 212. In the present embodiment, the reason why the shape of the balloon (212,213) has been changed as described above is to prevent the rupture of the balloon (212,213) when the balloon (212,213) is expanded.

More particularly, when the balloon (212,213) is expanded by the injection of liquid, the second expansion unit 213 having a relatively small diameter is first expanded. An interval between the second expansion unit 213 and a second shaft 220 may be, for example, 0.1 to 1.0 mm. Accordingly, if the second expansion unit 213 is first expanded in the process of the balloon (212,213) being expanded, the first expansion unit 212 is uniformly expanded. Since the diameter of the first expansion unit 212 is always greater than that of the second expansion unit 213, wall tension applied to a surface of the balloon is much smaller in the second expansion unit 213 than in the first expansion unit 212 in accordance with LaPlace' law. Although a modification is applied to the second expansion unit 213 so that second expansion unit 213 is attached to some of the shaft, a rupture phenomenon can be minimized.

Referring to FIG. 6, the rear end of the second expansion unit 213 on the upper part of the second expansion unit 213 is attached to the second shaft 220. The rear end of the upper part of the second expansion unit 213 may be attached across the second shaft 220 and a first shaft 210 as in FIG. 6. In this state, a wire discharge hole 224 that penetrates the upper part of the second expansion unit 213 and the second shaft 220 is formed. If the second expansion unit 213 is attached in the same way, the balloon (212,213) can be uniformly expanded because an interval between the second shaft 220 and the second expansion unit 213 can be minimized.

Furthermore, in an embodiment of the present invention, a core wire (not shown) that is present in the first shaft 210 (i.e., mid-shaft) or connected to the second shaft 220 in the first shaft 210 is necessary in order to prevent a bending phenomenon occurring when force is applied to put the balloon at a point where the first shaft 210 and the second shaft 220 are met, that is, a portion from which the guide wire W exits, and to improve the pushability of the balloon catheter when fabricating the balloon catheter. The core wire may be made of polymer having different strength in addition to metal, such as stainless steel or nitinol.

The scope of the present invention is not limited to the aforementioned embodiments, but is defined by the claims. It is evident to those skilled in the art to which the present invention pertains that the present invention may be modified and adapted in various ways within the scope of the claims.

The invention claimed is:

1. A balloon catheter comprising:
   a first shaft;
   a second shaft coaxially connected to a front end of the first shaft without overlapping with the first shaft and having same diameter as the first shaft;
   a blocking medium installed at a portion where the first shaft and the second shaft are connected;
   a balloon having upper and lower parts, wherein front ends of the upper and lower parts of the balloon are attached to a front end of the second shaft, a rear end of the upper part of the balloon is attached to a rear end of the second shaft, a rear end of the lower part of the balloon is attached to the front end of the first shaft;
   an expansion lumen formed within the first shaft and supplied with liquid necessary to expand the balloon;
   a guide wire lumen formed within the second shaft and having a guide wire pass through the guide wire lumen, wherein the guide wire lumen is separated and blocked from the expansion lumen by the blocking medium;
   a pressure injection port formed in the front end of the first shaft, wherein the pressure injection port is formed between the blocking medium and the rear end of the lower part of the balloon, the liquid is injected into the balloon through the pressure injection port;

a wire discharge hole formed in the rear end of the second shaft, wherein the guide wire is discharged through the wire discharge hole;

a radiopaque marker formed in at least one of the first shaft and the second shaft; and a hub installed at a rear end of the first shaft and combined with a pressurization device for supplying the liquid, wherein the blocking medium is installed between the wire discharge hole and the pressure injection port.

2. The balloon catheter of claim 1, wherein the balloon comprises:

a first expansion unit; and a second expansion unit having a smaller diameter than the first expansion unit.

3. The balloon catheter of claim 2, wherein a rear end of an upper part of the second expansion unit is attached to the second shaft wherein the wire discharge hole penetrates the second expansion unit and the second shaft.

4. The balloon catheter of claim 3, wherein the rear end of the upper part of the second expansion unit is attached across the second shaft and the first shaft.

5. The balloon catheter of claim 1, further comprising a core wire connected to the first shaft or connected from the first shaft to the second shaft.

6. The balloon catheter of claim 5, wherein the core wire is made of any one of stainless steel, nitinol, and polymer.

* * * * *